United States Patent [19]

Wong-Staal et al.

[11] Patent Number: 5,063,053

[45] Date of Patent: Nov. 5, 1991

[54] ISOLATION AND PURIFICATION OF THE R18 ANTIGEN OF HTLV-III

[75] Inventors: Flossie Wong-Staal, Rockville, Md; Pranab K. Chanda, Paoli; John Ghrayeb, Thorndale, both of Pa.

[73] Assignee: The United States of America as represented by the Department of Health & Human Services, Washington, D.C.

[21] Appl. No.: 556,999

[22] Filed: Jul. 25, 1990

Related U.S. Application Data

[62] Division of Ser. No. 920,780, Oct. 20, 1986, Pat. No. 4,963,497.

[51] Int. Cl.$^5$ ............... A61K 39/21; A61K 39/42; C07K 15/06
[52] U.S. Cl. ................... 424/89; 530/387; 530/350; 424/86
[58] Field of Search ............ 530/387, 350; 424/85.8, 424/88, 86, 89

[56] References Cited

U.S. PATENT DOCUMENTS 4,912,030  3/1990  Weiss et al. ............... 435/5

OTHER PUBLICATIONS

Pescador et al., Science vol. 227, 484–492.

*Primary Examiner*—Margaret Moskowitz
*Assistant Examiner*—Lila Feissee
*Attorney, Agent, or Firm*—Mishrilal Jain

[57] ABSTRACT

The isolation and purification of a newly discovered gene of the AIDS virus, HTLV-III, which encodes a portein which is immunogenic and recognized by sera of some HTLV-III seropositive people. Furthermore, the gene is highly conserved among all known HTLV-III isolates and exhibits a polymorphism at the 3' end which distinguishes molecular clones of the HTLV-IIIB cell line from viral genomes of related viruses.

3 Claims, 2 Drawing Sheets

ISOLATION AND PURIFICATION OF THE R18 ANTIGEN OF HTLV-III

This is a divisional of application Ser. No. 06/920,780, filed Oct. 20, 1986, now U.S. Pat. No. 4,963,497, filed Sept. 16, 1991.

BACKGROUND OF THE INVENTION

The present invention is the isolation and purification of a newly discovered gene of the AIDS virus, HTLV-III, which encodes a protein which is immunogenic and recognized by sera of some HTLV-III seropositive people. Furthermore, the gene is highly conserved among all known HTLV-III isolates and exhibits a polymorphism at the 3' end which distinguishes molecular clones of the HTLV-IIIB cell line from viral genomes of related viruses (i.e., other HTLV-III isolates, LAV, ARV, etc.). Also, the gene or the gene product(s) may be suitable targets for antiviral therapy.

Four distinct isolates of acquired immune deficiency syndrome (AIDS) virus have been previously characterized in detail:

HTLV-III$_{RF}$ was obtained from a 25-year-old black Haitian man who immigrated to the United States in 1980. HTLV-III$_B$ denotes a group of very related viruses obtained in 1983 from several different patients with AIDS or ARC (AIDS related complex) from the New York City area in 1983. LAV-1a was obtained from a biopsied lymph node of a French homosexual man with lymphadenopathy syndrome who had over 50 different sexual partners per year and had travelled to many countries including the United States. ARV-2 was isolated from the peripheral blood of a homosexual man from San Francisco in 1984, one month before the diagnosis of AIDS was established. Representative clones comprising the full-length genomes of each of these viruses have been described and the nucleotide sequence published (see, for example, Ratner et al., *Nature,* Vol. 313, pages 277–284,, 1985).

Human T-cell Lymphotropic Virus Type III (HTLV-III), the etiological agent of Acquired Immune Deficiency Syndrome (AIDS), is now known generically as human immunodeficiency virus (HIV), is a member of the retrovirus family. However, the complexity of its genomic structure is unprecedented among retroviruses. In addition to the three structural genes (gag, pol, and env) in common with other retroviruses, four additional genes have already been identified (sor, 3'orf, and tat-III). Two of these, sor and 3'orf, were originally identified as open reading frames by nucleotide sequence studies and have been verified to encode serologically reactive proteins of 23 kd and 27 kd, respectively. Both of these gense appear to be dispensible for production of infectious cytopathic virions, although mutants lacking the sor gene are greatly compromised in the level of virus production. The transactivator gene (tat-III) was identified functionally by the capacity of its product to enhance expression of genes linked to the HTLV-III long terminal repeat (LTR). It is transcribed from three discontiguous segments of the HTLV-III genome into a 2.0 kb mRNA. The resultant protein (p14) is requisite for virus replication, and its level of expression directly correlates with the level of virus proteins produced, but not necessarily viral mRNA expression. Recently, a seventh viral gene product was found to be engendered by the same spliced mRNA as tat-III, but utilizes an alternate reading frame [Feinberg et al, *Cell,* 46:807–817 (1986); and Sodroski et al, *Nature,* 321:412–417 (1986)]. It is believed that the function of this gene is either to reverse an intrinsic block on the translation of HTLV-III gag and env mRNA into proteins, or to regulate the relative amounts of HTLV-III genomic and spliced subgenomic mRNA. If the former function is correct, the gene will be named art (anti-repressor transactivator); if the latter is correct, the gene will be named trs (trans-acting regulator of splicing). While the major effects of both tat-III and art/trs are post-transcriptional, HTLV-III-infected cells also synthesize a transcriptional activator specific for transcription from its own LTR (Okamoto and Wong-Staal, *Cell,* in press). This viral factor, whose location on the viral genome is still unknown, may be distinct from tat-III.

Inspection of the nucleotide sequences of diverse HTLV-III isolates revealed at least two other open reading frames that can potentially encode proteins of 80–100 amino acids. One of these, referred to as R, is the subject of the present invention, and is highly conserved among HTLV-III isolates.

The HTLV-III genome is unusually complex for a retrovirus, possessing in addition to the replicative genes (gag, pol, and env) at least three extra genes (sor, tat, and 3'orf). Of these, the transactivator gene of HTLV-III (tat-III) has been determined and shown to be critical to virus replication. The sor and 3'orf genes, originally identified as open reading frames, have been shown to encode proteins which are immunogenic in vivo, but the function of these genes are, as yet, unknown.

MATERIAL INFORMATION DISCLOSURE

Methods for the detection of HTLV-III antibodies are disclosed in Gallo et al (#4,520,113).

The discovery of the isolation and purification of the R gene has not yet been disclosed in any publication. However, the following publications are deemed pertinent:

Ratner et al, *Nature,* 313:277–284 (1985) discloses the nucleotide sequencing data of HTLV-III.

Muesing et al, *Nature,* 313:430–458 (1985) discloses the nucleotide sequences of the gag, pol, and env genes, as well as 7 exons of the genome (including the sequences for the sor and 3'orf genes, originally identified as open reading frames).

Arya et al, *Science,* 229:69–73 (1985) discloses the tat-III gene.

Feinberg et al, *Cell,* 46:807–817 (1986) and Sodroski et al, *Nature,* 321:412–417 (1986) disclose the 7th gene, art/trs (anti-repressor transactivator/trans-acting regulator of splicing).

SPECIFIC DISCLOSURE OF THE INVENTION

Figure 1:
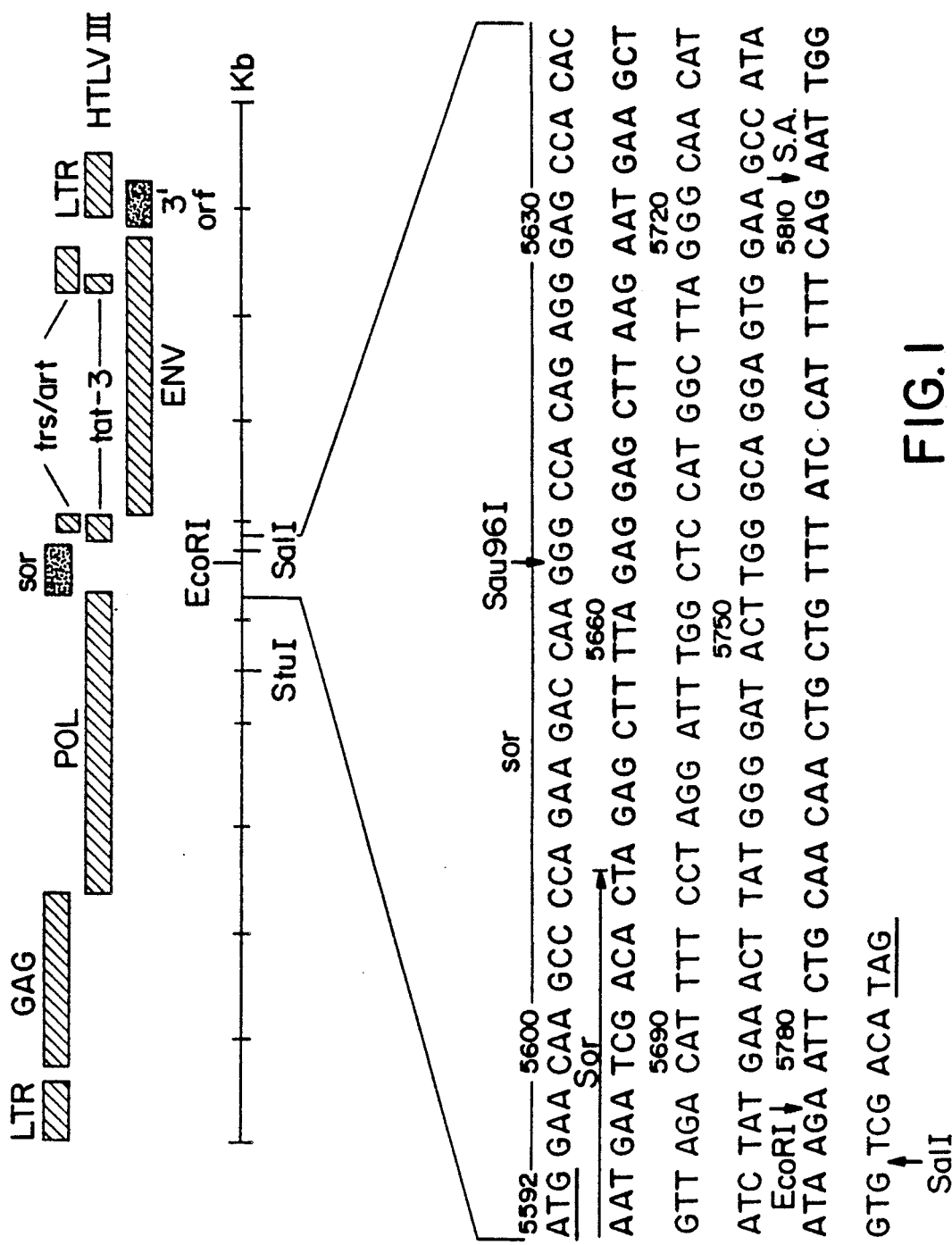
FIG. 1 depicts the R gene in relation to the nucleotide sequences of the HTLV-III genome.

The location of the R open reading frame in relation to the rest of the HTLV-III genome is shown in FIG. 1. The R gene overlaps with the sor gene, terminating before the first tat coding exon. Purified protein product from the R gene is produced by cleaving the HTLV-III DNA clone BH10 with Stu I and Sal I to produce a 379 bp Stu I-Sal I fragment. This fragment corresponds to nucleotides 5440-5777, using the numbering system described in Ratner et al, *Nature*, 313:277-284 (1985). The 379 bp fragment is then digested with Sau96 I to produce a 201 bp Sau96 I-Sal I fragment. The 201 bp fragment is then purified and subcloned into an expression vector. Expression vectors are well known by practitioners in the art—examples of expression vectors may be found in Maniatis et al, *Molecular Cloning*, Cold Spring Harbor Laboratory (1982). The peptide expressed from this expression vector is a 124 amino acid fusion protein containing 68 amino acids from the R region of HTLV-III, 43 amino acid residues at the amino terminus from the vector, and 13 amino acids at the carboxy terminus from the vector. The 68 amino acids derived from the R region represent all but 8 amino terminal and 2 carboxy terminal residues of this reading frame. Cell lysate obtained from expressor clone R18 reveals a specific protein band migrating as a 15 kd protein. This protein is purified to 95% purity by one chromatography step on a sephacryl S-300 column, followed by preparative SDS-polyacrylamide gel electrophoresis.

As shown in Table 2, the R gene is highly conserved among the nine proviruses for which sequence information is available. This is particularly true in the first 72 amino acids, where less than 9% divergence is observed even among isolates which differ by greater than 10% in their gag genes and greater than 20% in their env genes. The carboxy terminus of the R gene exhibits another interesting phenomenon. All four clones derived from the HTLV-IIIB cell line (HXB-2, BH10, BH5, and H9$_{pv}$) contain a termination codon after amino acid 77. The rest of the clones derived from LAV/-BRU, ARV, HAT3, ELI and MAL all differ from the HTLV-IIIB clones in amino acids 73-77 (due to a frame shift which also results in an extension of 18 or 19 amino acids.

Nucleotide sequences of several HTLV-III/LAV isolates show amino acid sequence variability between viral isolates from different individuals and between sequential isolates from one individual. This variability is clustered in the envelope protein and particularly in gp120, and recent evidence indicates that some neutralizing antibodies are virus type-specific. For example, antisera to gp120 isolated from the HTLV-III$_B$ isolate does not neutralize the divergent RF isolate, whereas neutralizing antibody from an AIDS patient blocks infectivity of both isolates. In addition, the presence of type-specific epitopes was shown by selection of resistant HTLV-III/LAV isolates by the passage of one sensitive isolate in the presence of neutralizing antibodies. The resistant isolates are resistant to the selecting antibodies but sensitive to neutralizing antibodies from other patients.

Whereas the variable regions of the exterior envelope proteins of the different HTLV-III/LAV viruses possess properties typical of antigenic epitopes, the conserved regions generally do not since they are generally hydrophobic and lack beta turns. An exception to this is a stretch of 45 amino acids immediately 5' to the envelope precursor clip site. This region is hydrophilic, contains numerous beta turns, and is highly conserved in all four viruses; experiments have shown that it is both immunogenic and broadly cross-reactive.

The finding of genomic variation primarily in exterior envelope sequences corresponding to predicted antigenic epitopes of different AIDS viruses suggests that immune pressures may be important in the selection of variant viral strains. It has been shown [Gonda et al., *Science*, Vol. 27, pages 173-177 (1985) and Shaw et al., *Science*, Vol. 27, pages 177-182 (1985)]that HTLV-III is significantly related in its nucleotide sequence, morphology, and biological behavior to visna virus, a member of the lentivirus family. This virus, as well as another lentivirus, equine infectious anemia virus (EIAV), appears to avoid elimination by host neutralizing antibodies as a result of divergence in its envelope glycoproteins.

One embodiment of the present invention is that the R gene is highly conserved in the first 72 amino acids, and yet is polymorphic at the carboxy terminus. In particular, this confers the ability of the R gene and the R gene product(s) to distinguish all clones of the HTLV-IIIB cells from all other existing virus isolates (or the clones derived from the isolates). The R gene is therefore suitable for use as another target of antiviral therapy. Additionally, this shows that the HTLV-III B viruses and LAV are derived from distinct lineages.

In the preferred embodiment, a Stu I-Sal I fragment from the BH10 clone of Human T-cell Lymphotropic Virus Type III is isolated and further digested with Sau 96 I. The 201 bp Sau 96 I-Sal I fragment is purified, then treated with DNA polymerase (Klenow fragment) in the presence of all four dNTP's, and ligated into the REV expression vector which had been previously digested with Sma I [the expression vector was obtained from Dr. S. Putney at Repligen, and described in Grayeb et al, *DNA*, 5:93–99 (1986)]. The ligated DNA is used to transfect *E. coli* strain SB221; a colony designated R18 contains the plasmid with the R gene sequences in the correct orientation. As is readily apparent to practitioners in the art, many slight deviations in the process noted above may be made without sacrificing the end result. Also, it will be apparent to practitioners in the art that other methods of separating the R gene may be used, now that the location of the gene is known.

One method of expression of the R protein in *E. coli* and subsequent purification of the protein is disclosed in Example 3.

Any of a large number of available host cells may be used in the combinations of this invention. The selection of a particular host is dependent upon a number of factors recognized by the art. These include, for example, compatability with the virus, toxicity of proteins encoded by the virus, ease of recovery of the desired virus or protein product, expression characteristics, biosafety, and costs. A balance of these factors must be struck with the understanding that not all hosts may be equally effective for expression of a particular recombinant DNA molecule.

Prior to the present invention, AIDS virus variants were propagated in an HT parental cell line, H9. This cell line, as well as other cell lines capable of immortalizing AIDS virus variants are described in Popovic et al, *Science*, 224:497 (1984) and Sarngadharan et al, *Science*, 224:506 (1984). Of critical concern is evidence that the T-cell tropism of the virus may be acquired behavior resulting from the continual propagation of the virus in T4+cells (particularly, H9 cells) both in vitro and in vivo. Quantitative titration of an $HTLV\text{-}III_B$ isolate on T-cells and M/M cells showed a 10,000-fold greater susceptibility of OKT4+T-cells than M/M cells. Limited evidence suggests that cells other than T-lymphocytes can be infected by the virus. It has been demonstrated that some rare B lymphocytes and a neoplastic cell line of monocyte-macrophage origin (both of which express T4 antigen) can be infected in vitro with HTLV-III/LAV. See Montagnier et al, *Science*, Vol. 225, p. 63 (1984); Dalgleish et al, *Nature*, Vol. 312 p. 763 (1984); and Levy et al, *Virology*, Vol. 147, p. 441 (1985). It has also been shown that HTLV-III/LAV sequences exist within the DNA and messenger RNA of brain tissues recovered from neurosymptomatic AIDS patients.

Another embodiment of the present invention is the production of antibodies, both polyclonal and monoclonal, which bind to the R gene sequences. Antibody molecules appear in the blood serum of an animal or human in response to an injection of an antigen, a protein, or another macromolecule foreign to the host species. Accordingly, the present invention—the R gene, the protein encoded by the R gene, or segments of the R gene—may be used as an antigen in the production of antibodies. In the preferred method, rabbits produce the antibodies of the present invention by hyperimmunizing them with an R gene antigen.

Monoclonal antibodies which specifically bind to the R gene region are also within the scope of the present invention. Using the well-known technique of Kohler and Milstein, "immortal" clones of cells making single antibody specificities are produced by fusing normal antibody-forming cells with an appropriate B-cell tumor line. Hybridomas are formed which may be selected out in a tissue culture medium which fails to support growth of the parental cell types, or by successive dilutions or by plating out. The single clones thus produced are then propagated in spinner culture or grown in the ascitic form in mice.

One skilled in the art will also recognize that the present invention may be subject to a variety of processes well known in the art. Some of these include molecular cloning; immortalization in a suitable host cell; detective, diagnostic, and prognostic test kits; or in the production of synthetic peptides.

DEFINITIONS

The following are the definitions of words used in the specification and claims.

ANTIBODY: serum protein produced in response to an immunogen.

ANTIGEN: substance capable of reacting with its specific antibody.

CLONING VEHICLE (VECTOR): A plasmid, phage DNA or other DNA sequence which is able to replicate in a host cell, characterized by one or a small number of endonuclease recognition or restriction sites at which such DNA sequences may be cut in a determinable fashion without attendant loss of an essential biologiocal function of the DNA, e.g., replication, production of coat proteins, loss of promoter or binding sites, and which contain a marker suitable for identifying the transformed cells (usually tetracycline resistance or ampicillin resistance). DNA SEQUENCE: A linear array of nucleotides connected one to the other by phosphodiester bonds between the 3' and 5' carbons of adjacent pentoses.

EXPRESSION: The process undergone by a structural gene to produce a polypeptide. This is a combination of transcription and translation.

EXPRESSION CONTROL SEQUENCE: A sequence of nucleotides that controls and regulated expression of genes when operatively linked to those genes.

GENOME: The entire DNA of a cell or virus. It includes the structural genes coding for the polypeptides of the substance, as well as operator, promoter, and ribosome binding and interaction sequences.

IMMUNOGEN: syn with antigen; more accurate—substance capable of eliciting an immune response.

NEUCLEOTIDE: A monomeric unit of DNA or RNA consisting of a sugar moiety (pentose), a phosphate, and a nitrogenous hetrocyclic base. The base is linked to the sugar moiety via the glycosidic carbon (1' carbon of the pentose) and the combination of the base and the sugar is a nucleoside. The base characterizes the nucleotide. The four DNA bases are adenine (A), guanine (G), cytosine (C), and thymine (T). The four RNA bases are A, G, C, and uracil (U).

RECOMBINANT DNA MOLECULE OR HYBRID DNA: A molecule consisting of segments of DNA from different genomes (the entire DNA of a cell or virus) which have been joined end-to-end outside of living cells and have the capacity to infect a host cell and be maintained therein.

STRUCTURAL GENE: A DNA sequence which encodes through its template or mesenger RNA a sequence of amino acids characteristic of a specific polypeptide.

TRANSCRIPTION: The process of producing mRNA from a structural gene.

TRANSLATION: The process of producing a polypeptide from mRNA.

EXAMPLES

Example 1

Figure 2:
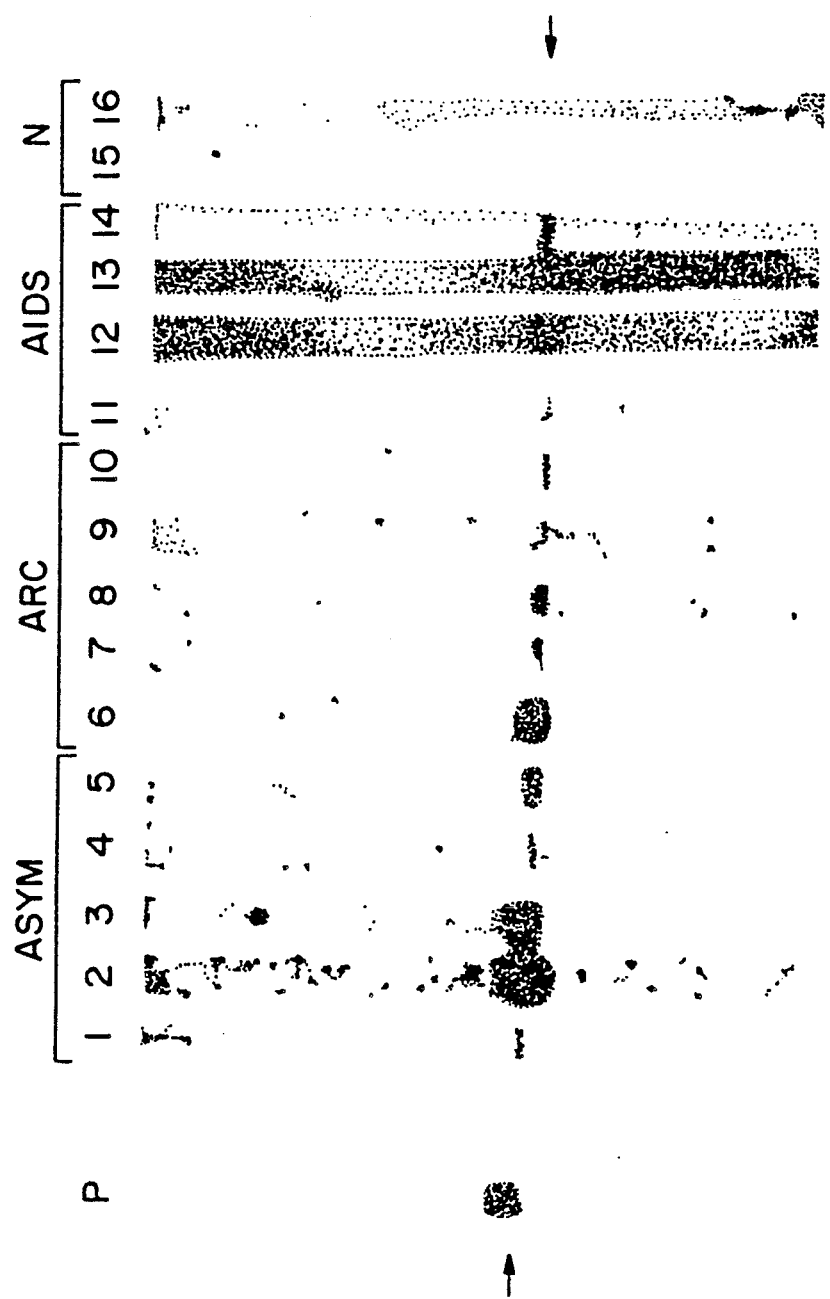
FIG. 2 is the Western immunoblot strip assay of serological detection of the R gene by patients' sera.

Over one hundred sera samples were examined for the detection of antibodies which specifically bind to the R 18 protein of the present invention. The results are summarized in Table 1. None of the 50 samples collected from healthy individuals showed positive reactivity against the R 18 protein. In contrast, a significant percentage of sera samples from known HTLV-III-infected individuals (as determined by serological reactivity against gag (p24) and/or env (gp41) proteins) tested positive against the R 18 protein. This result indicates that the R region of the genome encodes a protein which is immunoreactive. When the positive sera were broken down into asymptomatic carriers, ARC and AIDS patients, there appears to be a decline in both the frequency and titer of positive sera with progression of the disease (see Table 1 and FIG. 2 for representative Western Blot results).

EXAMPLE 2

In an attempt to assess the role of the tat-III gene, one mutant was constructed with an EcoRI-Sal I deletion which removed the splice acceptor site of the tat-III mRNA. As shown in FIG. 1, this mutant also deletes 15 amino acids on the carboxy end of the R gene. This mutant was able to transcribe the appropriate viral mRNA species at normal levels, but was severely compromised at the level of virion production, a property which was attributed, at the time, to the reduced tat-III activity. Indeed, complementation with bacterially expressed tat-III protein partially restored virus expression. This result argues that the R gene, like the 3' orf gene, is not required for virus replication, but may play a role in the in vivo pathogenesis of the virus.

EXAMPLE 3

For purification of the R protein, 6 liters of R18 cells were cultured for eight hours in L broth containing 100 ug/ml ampicillin. The cells were harvested and resuspended in a volume of 50 mM Tris-HCl pH 8.0, 1 mM PMSF equivalent to half their wet weight. The cell suspension was then treated with lysozyme (5 mg(ml) for 1 hour at 37° C. and disrupted using a Bead-Beater. The R18 protein present in the insoluble material after cell lysis was extracted in 50 mm Tris-HCl pH 8.0 containing 1 m sodium chloride, 8M urea, and 10 mM dithiothreitol, and applied to a sephacryl S-300 column. Fractions containing the R18 protein were pooled and concentrated. The R18 protein, 70% pure, was further purified by preparative SDS-polyacrylamide gel electrophoresis. The gel purified protein was >95% pure.

TABLE 1

Prevalence of Antibodies Against the R-Gene Product of HTLV-III Infected Patients

| Clinical Status | Number Tested | Number Positive | Percent Positive |
| --- | --- | --- | --- |
| Healthy donors | 50 | 0 | 0 |
| Asymptomatic infected patients* | 15 | 7 | 47 |
| ARC* | 38 | 16 | 42 |
| AIDS* | 29 | 5 | 17 |

*All these sera were positive for antibodies to p24 and/or gp 41

TABLE 2

Alignment of the R-Gene Protein Sequence

Clone*[1]

| | | | | | |
| --- | --- | --- | --- | --- | --- |
| BH10 | meqapedqgp | qrephnewtl | elleelknea | vrhfpriwlh | glygqhiyety |
| BY5 | | k | | | |
| HXB2 | | | | | |
| H9pf | | | | | |
| ARV2 | | y | r | p | s y |
| LAV | | | | | |
| ELI | a | y a | s | | s |
| MAL | a | | q | | s |
| HAT3 | | y | s | l | s |
| BH10 | gdtwagveai | irilqqllfi | hfqnwvst* | | |
| BH5 | | | * | | |
| HXB2 | | | * | | |
| H9pv | | | * | | |
| ARV2 | | | rigcqhsr | igiiqqrrqr | rngasrs* |
| LAV | | | rigcrhsr | igvtqqrrar | —ngasrs* |
| ELI | v | | rigcqhsr | igiirqrrar | —ngssrs* |
| MAL | e | s | rigcqhsr | igitrqrrar | —ngssrs* |
| HAT3 | | | eigcqhsr | igitrqrrar | —ngasrs* |

*BH10, BH5 Ratner et al. Nature 313:277-284 (1985); HXB2, Ratner et al. unpublished; H9pv Muesing et al. Nature, 313:430-458 (1985); ARV2 Sanchez-Pescador et al. Science, 227:484-492 (1985); LAV Wain-Hobson et al. Cell, 40:9-17 (1985); ELI, MAL Alizon et al. Cell, 46:63-74 (1986); HAT3 Starcich et al. Cell, 45:637-648 (1986).

a, alanine; r, arginine; n, asparagine; d, aspartic acid; c, cysteine; q, glutamine; e, glutamic acid; g, glycine; h, histidine; i, isoleucine; l, leucine; k, lysine; m, methionine; f, phenylalanine; p, proline; s, serine; t, threonine; w, tryptophan; y, tyrosine; v, valine.

We claim:

1. An isolated, more than 95% pure R18 antigen encoded by the R gene of HTLV-IIIB virus as shown in FIG. 1A.
2. A composition, comprising an immunoreactive concentration of the R18 antigen of claim 1.
3. An isolated antibody free, other blood proteins which binds to which which the antigen of claim 1.